United States Patent [19]

Deguchi et al.

[11] 4,359,365

[45] Nov. 16, 1982

[54] METHOD OF PURIFICATION OF β-PHENYLETHYL ALCOHOL

[75] Inventors: Takashi Deguchi, Kusatsu; Masahiro Usui; Yasuhiko Higashio, both of Ichihara, all of Japan

[73] Assignee: Sumitomo Chemical Company, Limited, Osaka, Japan

[21] Appl. No.: 194,859

[22] Filed: Oct. 7, 1980

[30] Foreign Application Priority Data

Oct. 16, 1979 [JP] Japan .................................. 54-133764
Nov. 28, 1979 [JP] Japan .................................. 54-154752
Jun. 30, 1980 [JP] Japan .................................. 55-89723

[51] Int. Cl.³ .......................... B01D 3/36; B01D 3/40; C07C 29/80
[52] U.S. Cl. ........................................ 203/55; 203/56; 203/64; 203/84; 203/85; 203/96; 568/810
[58] Field of Search ................ 568/715, 814, 810; 203/92, 93, 95-97, 55, 56, 64, 71, 73, 78, 84, 76, 79, 83, 85

[56] References Cited

U.S. PATENT DOCUMENTS

| | | | |
|---|---|---|---|
| 1,698,932 | 1/1929 | Britton | 568/810 |
| 1,752,365 | 4/1930 | Britton | 568/810 |
| 1,944,958 | 1/1934 | Valik et al. | 568/810 |
| 2,052,881 | 9/1936 | Klipstein et al. | 568/810 |
| 2,068,415 | 1/1937 | Klipstein | 568/810 |
| 2,114,286 | 4/1938 | Britton | 568/810 |
| 2,185,141 | 12/1939 | Britton et al. | 568/715 |
| 2,552,412 | 5/1951 | Drout et al. | 203/55 |
| 2,848,503 | 8/1958 | Fenske | 568/810 |
| 3,579,593 | 5/1971 | Wood | 568/814 |

*Primary Examiner*—Wilbur L. Bascomb, Jr.
*Attorney, Agent, or Firm*—Birch, Stewart, Kolasch & Birch

[57] ABSTRACT

A method of purification of crude β-phenylethyl alcohol to give a highly pure β-phenylethyl alcohol suitable as a perfume, which comprises subjecting the crude β-phenylethyl alcohol to azeotropic distillation in the presence of an azeotropic solvent selected from water, an alkylene glycol, an alkylene glycol monoalkyl ether and a mixture of two or more kinds of these solvents, or extractive distillation in the presence of an extractive solvent selected from glycerine, an alkylene glycol, a polyalkylene glycol, an alkylene glycol monoalkyl ether, a polyalkylene glycol monoalkyl ether and a mixture of two or more kinds of these solvents.

11 Claims, 2 Drawing Figures

METHOD OF PURIFICATION OF β-PHENYLETHYL ALCOHOL

The present invention relates to a method of purification of β-phenylethyl alcohol. More particularly, it relates to an improved method for obtaining pure β-phenylethyl alcohol having excellent fragrance from crude β-phenylethyl alcohol by distilling it in the presence of a specific solvent.

β-Phenylethyl alcohol has widely been used as a rosy perfume in various fields such as detergents, toiletries, or the like. For this purpose, it should have a high purity and high quality and fragrance. Generally, when a perfume is contaminated with even a slight amount of impurities which give undesirable effect on the essential fragrance thereof, it significantly loses its value as a product. Thus, it is very important to pay careful attention to the purification of perfume.

β-Phenylethyl alcohol has hitherto been purified by various methods, for example, by derivating β-phenylethyl alcohol to borate or an organic acid ester thereof, by adsorbing the impurities onto silica gel, or by distilling with a multistage fractionating column. However, these known methods have some drawbacks and hence are not necessarily suitable as an industrial purification method. According to the esterification method, it includes steps of esterification of β-phenylethyl alcohol and of hydrolysis of the resulting ester, and further, the acid must be used circularly. Thus, this method is not suitable from economical viewpoint. The method of adsorbing impurities has less purification effect and also has a problem in that silica gel should repeatedly be used after regeneration. The distillation method can hardly give the desired β-phenylethyl alcohol having satisfactorily high quality when the crude β-phenylethyl alcohol contains impurities having close boiling point or azeotropic impurities, even by using a highly multistage fractionating column.

The present inventors have intensively studied the purification of β-phenylethyl alcohol without using specific and complicated apparatus or procedure. As a result, it has been found that impurities having offensive smells can selectively be removed from crude β-phenylethyl alcohol merely by distilling the crude β-phenylethyl alcohol in the presence of a specific solvent.

An object of the present invention is to provide an improved method of purification of β-phenylethyl alcohol by a simple procedure without using any complicated apparatus. Another object of the invention is to provide a highly pure β-phenylethyl alcohol which is suitable as a perfume for various products. These and other objects and advantages of the present invention will be apparent to persons skilled in the art from the following description.

The purification method of the present invention can be carried out by subjecting crude β-phenylethyl alcohol to azeotropic distillation in the presence of a specific solvent (hereinafter called "the azeotropic solvent") having lower boiling point than β-phenylethyl alcohol or extractive distillation in the presence of a specific solvent (hereinafter "the extractive solvent") having higher boiling point than β-phenylethyl alcohol.

The azeotropic solvent used in the azeotropic distillation can be selected from the group consisting of water, an alkylene glycol, an alkylene glycol monoalkyl ether and a mixture of two or more thereof. The extractive solvent used in the extractive distillation can be selected from the group consisting of glycerine, an alkylene glycol, a polyalkylene glycol, an alkylene glycol monoalkyl ether, a polyalkylene glycol monoalkyl ether, and a mixture of two or more thereof. Consequently, in the present specification, "azeotropic distillation" means a distillation wherein the used solvent is taken out in the form of distillate together with the impurities and the desired β-phenylethyl alcohol is obtained as the remaining residue, and "extractive distillation" means a distillation wherein the impurities are distilled off and the desired β-phenylethyl alcohol is taken out from the bottom of the vessel together with the used solvent. Depending on the kind of solvent used, either distillation method is adopted.

The alkylene glycol used as the solvent in the present invention includes alkane diols having 2 to 15 carbon atoms in the alkane moiety and cycloalkane diols having 5 to 10 carbon atoms in the cycloalkane moiety, for example 1,2-ethanediol, 1,2-propanediol, 1,3-propanediol, 1,3-butanediol, 1,4-butanediol, 2,3-butanediol, 1,2-pentanediol, 1,5-pentanediol, 1,2-hexanediol, 1,3-hexanediol, 1,6-hexanediol, 1,2-heptanediol, 1,7-heptanediol, 3,4-heptanediol, 1,2-octanediol, 2,4-octanediol, 1,2-cyclohexanediol, 1,4-dimethylolcyclohexane, or the like. The alkylene glycol monoalkyl ether includes monoalkyl ethers of the above-mentioned alkylene glycols having 1 to 4 carbon atoms in the monoalkyl ether moiety, for example 2-hydroxyethyl methyl ether, 2-hydroxyethyl ethyl ether, 2-hydroxyethyl propyl ether, 2-hydroxyethyl butyl ether, 1,2-propanediol-1-methyl ether, 1,3-propanediol-1-ethyl ether, 1,3-butanediol-1-methyl ether, or the like. The polyalkylene glycol includes polyalkylene glycols having 4 to 30 carbon atoms in the alkylene moiety, for example diethylene glycol, triethylene glycol, tetraethylene glycol, dipropylene glycol, tripropylene glycol, tetrapropylene glycol, or the like. The polyalkylene glycol monoalkyl ether includes monoalkyl ethers of the above-mentioned polyalkylene glycols having 1 to 4 carbon atoms in the monoalkyl ether moiety, for example diethylene glycol monoethyl ether, triethylene glycol monoethyl ether, dipropylene glycol monoethyl ether, tripropylene glycol monomethyl ether, or the like.

The solvents may be used alone or in combination of two or more kinds thereof. Particularly suitable examples of the solvent are water, ethanediol, propanediols, butanediols, diethylene glycol, dipropylene glycol, a mixture of water and ethandiol, a mixture of water and a propanediol, and a mixture of water and a butanediol. Amount of the solvent is not critical, but it is usually used in an amount of 0.1 to 20 parts by weight, preferably 0.5 to 5 parts by weight, per 1 part by weight of the starting crude β-phenylethyl alcohol.

The solvents used in the present invention, i.e. water, glycerine, alkylene glycols, polyalkylene glycols, alkylene glycol monoalkyl ethers, and polyalkylene glycol monoalkyl ethers, have a particularly excellent selectivity for the purification of β-phenylethyl alcohol, and hence, can be used for the removal of impurities which can not be removed by the conventional fractionation using a multistage fractionating column.

The method of purification of β-phenylethyl alcohol of the present invention is illustrated with reference to the accompanying drawings.

Figure 1:
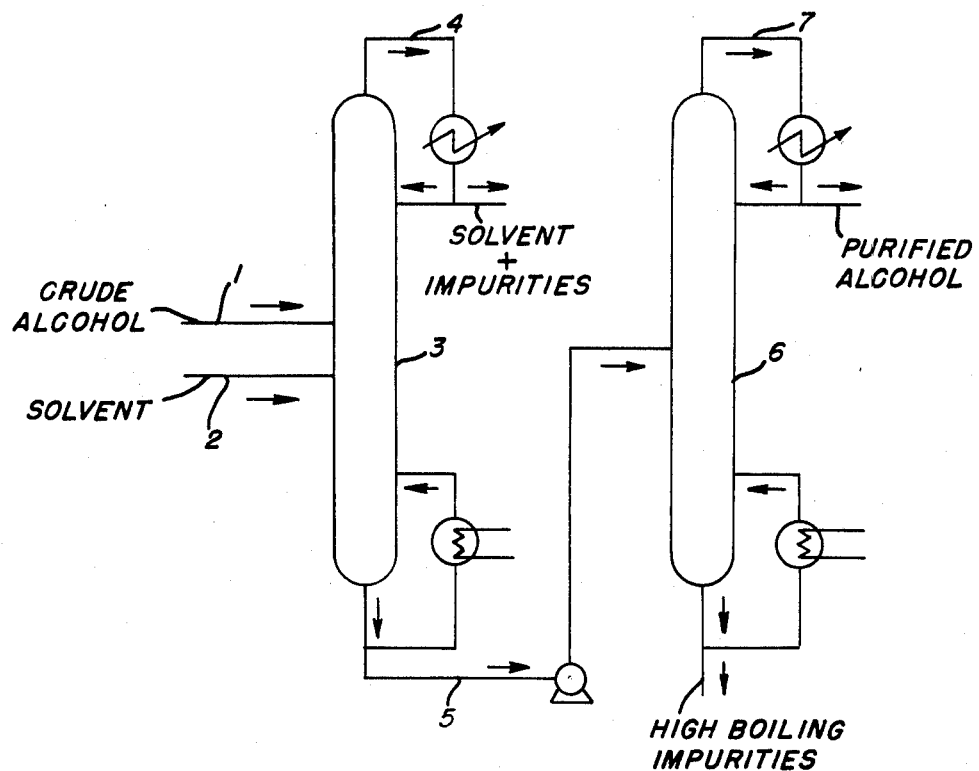
FIG. 1 shows a flow sheet of an embodiment of azeotropic distillation by the present invention.

Referring to FIG. 1, the azeotropic distillation is carried out as follows. The starting crude β-phenylethyl alcohol is charged into an azeotropic distillation column (3) having multiple plates via a supply pipe (1) which is provided at the middle of the distillation column (3). One of the azeotropic solvents such as water, an alkylene glycol or an alkylene glycol monoalkyl ether or a mixture of two or more thereof is charged into the distillation column (3) via a supply pipe (2) which is provided below the supply pipe (1). Alternatively, the starting crude β-phenyl-ethyl alcohol may be mixed with the solvent beforehand and charged into the azeotropic distillation column, in this case supply pipe (1) and (2) is of course the same one. These crude β-phenylethyl alcohol and solvent are supplied continuously. Azeotropic distillation is carried out in the azeotropic distillation column (3) under reduced pressure, and impurities having offensive smells are distilled off from a pipe (4) at the top of the column (3) together with the used azeotropic solvent having a high volatility. The distillate is cooled with a condenser and the condensed solvent is circulated into the column (3) at a fixed reflux ratio. From the bottom of the column (3), β-phenylethyl alcohol is taken out through a drain pipe (5), a part of which may be heated with a heater and circulated into the column (3). The β-phenylethyl alcohol thus taken out is sent to the middle of a rectification column (6) by pumping, wherein precise fractional distillation is carried out under reduced pressure. β-phenylethyl alcohol is distilled out through a pipe (7) at the top of the column (6) and is cooled with a condenser to give the desired pure β-phenylethyl alcohol, a part of which is circulated into the column (6) at a fixed reflux ratio. The distillation in the azeotropic distillation column and the rectification column is carried out under usual conditions, i.e. under reduced pressure (e.g. 1 to 750 mmHg), at a temperature of 50° to 200° C., and at a reflux ratio of 0.1 to 50.

Figure 2:
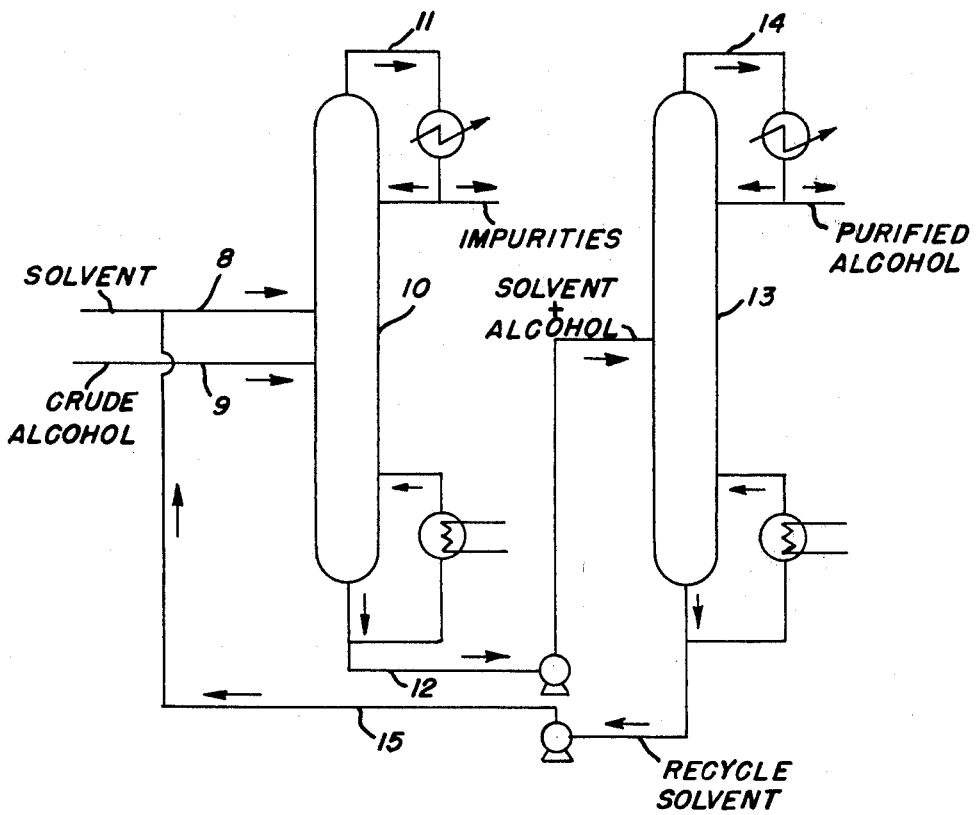
FIG. 2 shows a flow sheet of an embodiment of extractive distillation by the present invention.

Referring to FIG. 2, the extractive distillation is carried out as follows. The starting crude β-phenylethyl alcohol is charged into an extractive distillation column (10) via a supply pipe (9) which is provided at the middle of the column (10). One of the extractive solvent such as glycerine, an alkylene glycol, an alkylene glycol monoalkyl ether, a polyalkylene glycol or a polyalkylene glycol monoalkyl ether or a mixture of two or more thereof is charged into the extractive distillation column (10) via a supply pipe (8) which is provided above the pipe (9). Alternatively, the starting crude β-phenylethyl alcohol may be mixed with the solvent beforehand and charged into the extractive distillation column, in this case supply pipe (8) and (9) is of course the same one. These β-phenylethyl alcohol and solvent are supplied continuously. The extractive distillation is carried out in the extractive distillation column (10) under reduced pressure. The distillate comprising predominantly impurities having offensive smells and high volatility is distilled off from a pipe (11) at the top of the column (10). The distillate is cooled with a condenser and circulated into the column (10) at a fixed reflux ratio. From the bottom of the column (10), a mixture of β-phenylethyl alcohol and the solvent is taken out via a drain pipe (12), a part of which may be heated with a heater and circulated into the column (10). The mixture thus taken out from the column (10) is sent to a solvent recovering column (13) which is for example a multistage fractionating column by pumping, wherein the β-phenylethyl alcohol and solvent are separated each other by fractionating under reduced pressure. The distillate comprising predominantly β-phenylethyl alcohol thus separated is taken out from the top of the column (13) via a distillate pipe (14), and the distillate is cooled with a condenser to give pure β-phenylethyl alcohol and a part of the condensed distillate is circulated into the column (13) at a fixed reflux ratio. From the bottom of the column (13), the solvent is taken out via a drain pipe (15) and circulated into the supply pipe (8) as it is or after replacing partially with a fresh solvent. The distillation in the extractive distillation column and solvent recovering column is also carried out under usual conditions, i.e. under reduced pressure (e.g. 1 to 750 mmHg), at a temperature of 50° to 200° C., and at a refulx ratio of 0.1 to 50.

In the above flow sheets of FIGS. 1 and 2, the most suitable supplying position of the starting crude β-phenylethyl alcohol and the solvent to the azeotropic distillation column (3) and the extractive distillation column (10) is optionally determined, and the most suitable supplying position of β-phenylethyl alcohol to the rectification column (6) and of the mixture of β-phenylethyl alcohol and solvent to the solvent recovering column (13) is also optionally determined. Besides, as already described the azeotropic solvent and the extracting solvent may be charged into the column (3) or (10) respectively after mixing with the starting crude β-phenylethyl alcohol.

The above-mentioned procedure is carried out in continuous system, but the purification method of the present invention may also be carried out in batch system.

The purification method of the present invention may optionally be combined with other conventional purification methods, such as esterification method, silica gel adsorption method, fractionation method, a method of treatment with an acid or an alkali.

The starting crude β-phenylethyl alcohol applicable to the present invention may be any product obtained by conventional processes, such as reduction of styrene oxide with hydrogen, reaction of benzene and ethylene oxide, reduction of phenylacetic acid with hydrogen, oxidation of aromatic hydrocarbon compounds, or the like. The present invention is particularly useful for the purification of crude β-phenylethyl alcohol containing impurities having offensive smells and a boiling point close to that of β-phenylethyl alcohol.

The β-phenylethyl alcohol obtained by the present invention has no unpleasant smell and has a high quality suitable as a perfume.

The present invention is illustrated by the following Examples and Reference Examples, but it is not limited to the Examples.

EXAMPLE 1

A continuous azeotropic distillation was carried out in the system as shown in FIG. 1, wherein the azeotropic distillation column (3) had 50 plates and the rectification column (6) had 15 plates, and the distillation in both columns was carried out under reduced pressure of 100 mmHg.

The starting crude β-phenylethyl alcohol containing 6.5% by weight of impurities and having offensive smells was continuously charged into the azeotropic distillation column (3) at the rate of 150 parts by weight per hour via the supply pipe (1) which was provided at 20th plate from the top of the column. The azeotropic solvent, i.e. a mixture of 1,2-propanediol and water (mixed ratio, 1:1 by weight) was continuously charged into the column (3) at the rate of 300 parts by weight per hour via the supply pipe (2) which was provided at 40th plate from the top of the column. The distillate consisting of 1,2-propanediol, water and offensive smell components was distilled out from the distillate pipe (4) at the rate of 314 parts by weight per hour. From the bottom of the column (3), β-phenylethyl alcohol was taken out through the drain pipe (5) and supplied to the rectification column (6) at the position of 8th plate from the top of the column (6) and subjected to the rectification distillation. Purified β-phenylethyl alcohol was distilled out from the top of the column (6) through the distillate pipe (7) at the rate of 132 parts by weight per hour. The pure β-phenylethyl alcohol thus obtained had a purity of 99.9% and had no unpleasant smell, and hence the product is suitable for using as a perfume.

REFERENCE EXAMPLE 1

In the same manner as described in Example 1, the distillation was carried out by supplying crude β-phenylethyl alcohol containing 6.5% by weight of impurities and having offensive smells to the distillation column (3) at the rate of 150 parts by weight per hour via the supply pipe (1) which was provided at the 20th plate of the column. The distillate was taken out through the distillate pipe (4) at the rate of 14 parts by weight per hour. The liquid was taken out from the bottom of the column (3) via the drain pipe (5) and supplied to the rectification column (6) at the position of 8th plate from the top of the column and subjected to precise fractional distillation. β-phenylethyl alcohol was distilled out from the top of the column (6) through the distillate pipe (7) at the rate of 131 parts by weight per hour. The thus obtained β-phenylethyl alcohol had still offensive smells and did not have a quality suitable as a perfume.

EXAMPLE 2

The distillation was carried out by using the same apparatus as used in Example 1.

The starting β-phenylethyl alcohol containing 3.5% by weight of impurities and having offensive smells was continuously charged into the distillation column (3) at the rate of 150 parts by weight per hour via the supply pipe (1) which was provided at 20th plate from the top of the column. The azeotropic solvent, i.e. water was continuously charged into the column (3) at the rate of 300 parts by weight per hour via the supply pipe (2) which was provided at 40th plate from the top of the column. The distillate was taken out from the top of the column through the distillate pipe (4) at the rate of 315 parts by weight per hour. The liquid was taken out from the bottom of the column (3) via the drain pipe (5) and supplied to the rectification column (6) at the position of 8th plate from the top of the column and subjected to precise fractional distillation. β-phenylethyl alcohol was distilled out from the top of the column (6) through the distillate pipe (7) at the rate of 130 parts by weight per hour. The pure β-phenylethyl alcohol thus obtained had no unpleasant smell and had a high quality (purity: 99.8%) suitable as a perfume.

EXAMPLE 3

By using an apparatus as shown in FIG. 1, wherein the azeotropic distillation column (3) had 35 plates, the distillation was carried out.

A mixture of the starting crude β-phenylethyl alcohol containing 2.5% by weight of impurities and having offensive smells and 1,2-propanediol (mixed ratio, 1:2 by weight) was continuously charged into the azeotropic distillation column (3) at the rate of 300 parts by weight per hour via the supply pipe (1) which was provided at 20th plate from the top of the column and subjected to azeotropic distillation. A mixture of 1,2-propanediol and offensive smell components was distilled out from the top of the column (3) through the distillate pipe (4) at the rate of 208 parts by weight per hour. From the bottom of the column (3), β-phenylethyl alcohol was taken out through the drain pipe (5) and sent to the rectification column (6) at the position of 8th plate from the top of the column (6) and subjected to precise fractional distillation. The purified β-phenylethyl alcohol was distilled out through the distillate pipe (7) at the rate of 92 parts by weight per hour. The pure β-phenylethyl alcohol thus obtained had no unpleasant smell and had a high quality (purity: 99.7%) suitable for using as a perfume.

EXAMPLE 4

In the same manner as described in Example 3 using an azeotropic distillation column (3) having 35 plates, the distillation was carried out.

A mixture of the starting crude β-phenylethyl alcohol containing 3.0% by weight of impurities and having offensive smells and 1,2-propanediol-1-methyl ether (mixed ratio, 1:2 by weight) was continuously charged into the column (3) at the rate of 300 parts by weight per hour via the supply pipe (1) which was provided at 20th plate from the top of the column and subjected to azeotropic distillation. A mixture of 1,2-propanediol-1-methyl ether and offensive smell components was distilled out through the distillate pipe (4) at the rate of 206 parts by weight per hour. From the bottom of the column (3), β-phenylethyl alcohol was taken out through the drain pipe (5) and sent to the rectification column (6) at the position of 9th plate from the top of the column (6) and subjected to precise fractional distillation. The purified β-phenylethyl alcohol was distilled out through the distillate pipe (7) at the rate of 94 parts by weight per hour. The pure β-phenylethyl alcohol thus obtained had no unpleasant smell and had a high quality (purity: 99.4%) suitable as a perfume.

EXAMPLE 5

A continuous extractive distillation was carried out in the system as shown in FIG. 2, wherein the extractive distillation column (10) had 35 plates and the solvent recovering column (13) had 15 plates, and the distillation in both columns was carried out under reduced pressure of 100 mmHg.

The starting crude β-phenylethyl alcohol containing 3.0% by weight of impurities and having offensive smells was continuously charged into the extractive distillation column (10) at the rate of 100 parts by weight per hour via the supply pipe (9) which was provided at 25th plate from the top of the column (10). The extracting solvent, diethylene glycol was continuously charged into the column (10) at the rate of 200 parts by weight per hour via the supply pipe (8) which was provided at 10th plate from the top of the column (10). The distillate comprising predominantly offensive smell components was distilled out through the distillate pipe (11) at the top of the column at the rate of 5 parts by weight per hour. A mixture of β-phenylethyl alcohol and diethylene glycol was taken out through the drain pipe (12) and supplied to the solvent recovering column (13) at the position of 6th plate from the top of the column and subjected to fractionating distillation. Purified β-phenylethyl alcohol was distilled out through the distillate pipe (14) at the rate of 95 parts by weight per hour. From the bottom of the column (13), diethylene glycol was taken out through the drain pipe (15) at the rate of 200 parts by weight per hour. The pure β-phenylethyl alcohol thus obtained had no unpleasant smell and had a high quality (purity: 99.8%) suitable as a perfume.

REFERENCE EXAMPLE 2

By using the same apparatus as used in Example 5, the distillation was carried out.

The starting crude β-phenylethyl alcohol containing 3.0% by weight of impurities and having offensive smells was continuously charged into the extractive distillation column (10) at the rate of 100 parts by weight per hour via the supply pipe (9) which was provided at 25th plate from the top of the column and subjected to distillation under a reduced pressure of 100 mmHg. The distillate was taken out through the distillate pipe (11) at the rate of 5 parts by weight per hour. The liquid taken out from the bottom of the column (10) through the drain pipe (12) was sent to the column (13) at the position of 6th plate from the top of the column and subjected to fractionating distillation. β-Phenylethyl alcohol was distillated out from the top of the column via the distillate pipe (14) at the rate of 95 parts by weight per hour. The β-phenylethyl alcohol thus obtained had still offensive smells and did not have a quality suitable as a perfume.

EXAMPLES 6 AND 7

In the same manner as described in Example 5 except that the extracting solvents as shown in Table 1 were used, the distillation was carried out to give pure β-phenylethyl alcohol having no offensive smells and being useful as a perfume. The results are shown in Table 1.

TABLE 1

| | Example 6 | Example 7 |
|---|---|---|
| Crude β-phenylethyl alcohol | | |
| Content of β-phenylethyl alcohol | 97.5% | 98.0% |
| Content of impurities | 2.5% | 2.0% |
| Extracting solvent | Dipropylene glycol | Glycerine |
| Distillate from the top of the extractive distillation column (10) | 9 parts by weight per hour | 7 parts by weight per hour |
| Distillate from the top of the solvent recovering column (13) | 91 parts by weight per hour | 93 parts by weight per hour |
| Composition of the distillate from the top of the solvent recovering column (13) | | |
| β-Phenylethyl alcohol | 99.5% | 99.7% |
| Impurities | 0.5% | 0.3% |

EXAMPLE 8

In the same manner as described in Example 3, except that the extracting solvent as shown in Table 2 was used, the distillation was carried out. The results are shown in Table 2.

TABLE 2

| | |
|---|---|
| Starting crude β-phenylethyl alcohol | |
| Content of β-phenylethyl alcohol | 97.5% |
| Content of impurities | 2.5% |
| Azeotropic solvent | 1,2-Ethanediol |
| Distillate from the top of the azeotropic distillation column (3) | 210 parts by weight per hour |
| Distillate from the top of the fractionating distillation column (6) | 90 parts by weight per hour |
| Composition of the distillate from the top of the fractionating distillation column (6) | |
| β-Phenylethyl alcohol | 99.8% |
| Impurities | 0.2% |

EXAMPLE 9

In the same manner as described in Example 1, the distillation was carried out.

The starting crude β-phenylethyl alcohol containing 3.5% by weight of impurities and having offensive smells was continuously charged into the azeotropic distillation column (3) at the rate of 150 parts by weight per hour via the supply pipe (1) which was provided at 20th plate from the top of the column. The solvent, i.e. a mixture of ethylene glycol monomethyl ether and water (mixed ratio, 2:1 by weight) was continuously charged into the column (3) at the rate of 300 parts by weight per hour via the supply pipe (2) which was provided at 40th plate from the top of the column. The distillate was taken out through the distillate pipe (4) at the rate of 318 parts by weight per hour. The liquid taken out from the bottom of the column (30) through the drain pipe (5) was sent to the rectification column (6) at the position of 8th plate from the top of the column (6) and subjected to precise fractional distillation. β-Phenylethyl alcohol was distilled out from the top of the column (6) through the distillate pipe (7) at the rate of 127 parts by weight per hour. The pure β-phenylethyl alcohol thus obtained had no unpleasant smell and had a high quality (purity: 99.8%) suitable as a perfume.

What is claimed is:

1. A method of purification of crude β-phenylethyl alcohol, which comprises: introducing a mixture of crude β-phenylethyl alcohol and a solvent selected from the group consisting of water, glycerine, an alkylene glycol, a polyalkylene glycol, an alkylene glycol monoalkyl ether, a polyalkylene glycol monoalkyl ether and mixtures thereof into a distillation column; and distilling off impurities from the top of said column and removing β-phenylethyl alcohol from the bottom of said column.

2. A method according to claim 1, wherein said purification method is carried out by subjecting the crude β-phenylethyl alcohol to azeotropic distillation in an azeotropic distillation column in the presence of an azeotropic solvent selected from the group consisting of water, an alkylene glycol, an alkylene glycol monoalkyl ether and a mixture thereof.

3. A method according to claim 2, wherein β-phenylethyl alcohol is removed from said azeotropic distillation column and is then subjected to precise fractional distillation.

4. A method according to claim 1, wherein said purification method is carried out by subjecting the crude β-phenylethyl alcohol to extractive distillation in an extractive distillation column in the presence of an extractive solvent selected from the group consisting of glycerine, an alkylene glycol, a polyalkylene glycol, an alkylene glycol monoalkyl ether, a polyalkylene glycol monoalkyl ether and a mixture thereof.

5. A method according to claim 4, wherein β-phenylethyl alcohol is removed from said extractive distillation column and is then separated from the solvent in a solvent recovering column.

6. A method according to any one of claims 1, 2, 3, 4 or 5 wherein the alkylene glycol is a member selected from the group consisting of ethanediol, propanediol, butanediol, pentanediol, hexanediol, heptanediol, and octanediol.

7. A method according to any one of claims 1, 2, 3, 4 or 5, wherein the alkylene glycol monoalkyl ether is a member selected from the group consisting of 2-hydroxyethyl methyl ether, 2-hydroxyethyl ethyl ether, 2-hydroxyethyl propyl ether, 2-hydroxyethyl butyl ether, 1,2-propanediol-1-methyl ether, and 1,3-propanediol-1-ethyl ether.

8. A method according to any one of claims 1, 3 or 5, wherein the polyalkylene glycol is a member selected from the group consisting of diethylene glycol, triethylene glycol, tetraethylene glycol, dipropylene glycol, tripropylene glycol, and tetrapropylene glycol.

9. A method according to any one of claims 1, 3 or 5, wherein the polyalkylene glycol monoalkyl ether is a member selected from the group consisting of diethylene glycol monomethyl ether, triethylene glycol monoethyl ether, dipropylene glycol monoethyl ether, and tripropylene glycol monoethyl ether, and tripropylene glycol monomethyl ether.

10. A method according to any one of claims 1, 2, 3, 4 or 5, wherein the solvent is used in an amount of 0.1 to 20 parts by weight per 1 part by weight of the starting crude β-phenylethyl alcohol.

11. A method of purification of crude β-phenylethyl alcohol, which comprises:
introducing a mixture of crude β-phenylethyl alcohol and a solvent selected from the group consisting of water, glycerine, an alkylene glycol monoalkyl ether, a polyalkylene glycol monoalkyl ether and mixtures thereof into an azeotropic distillation column; and
subjecting said mixture to azeotropic distillation in said azeotropic distillation column and removing impurities and said solvent from the top of said azeotropic distillation column and removing the β-phenylethyl alcohol from the bottom of said azeotropic distillation column.

* * * * *